US008175590B2

(12) United States Patent
Hamel et al.

(10) Patent No.: US 8,175,590 B2
(45) Date of Patent: May 8, 2012

(54) SYSTEM FOR PREVENTING UNINTENDED ACTIVATION OF A MEDICAL DEVICE BY A PORTABLE REMOTE CONTROL CONSOLE

(75) Inventors: Andrew J. Hamel, San Mateo, CA (US); Brannon P. Wells, San Jose, CA (US); Michael G. Hilldoerfer, Sunnyvale, CA (US)

(73) Assignee: Stryker Corporation, Kalamazoo, MI (US)

( * ) Notice: Subject to any disclaimer, the term of this patent is extended or adjusted under 35 U.S.C. 154(b) by 445 days.

(21) Appl. No.: 12/283,808

(22) Filed: Sep. 16, 2008

(65) Prior Publication Data

US 2009/0080348 A1    Mar. 26, 2009

Related U.S. Application Data

(60) Provisional application No. 60/995,330, filed on Sep. 26, 2007.

(51) Int. Cl.
*H04M 3/00* (2006.01)

(52) U.S. Cl. ....... 455/419; 455/418; 455/420; 455/41.1; 455/41.2

(58) Field of Classification Search ....... 455/414.1–421, 455/456.1–457, 41.1–41.2; 340/870.16, 340/870.17, 870.19, 540, 815.6, 825.29; 398/106–114
See application file for complete search history.

(56) References Cited

U.S. PATENT DOCUMENTS

| | | | |
|---|---|---|---|
| 5,594,786 A | 1/1997 | Chaco et al. | |
| 6,314,297 B1 * | 11/2001 | Karl | 455/456.3 |
| 2002/0161317 A1 * | 10/2002 | Risk et al. | 602/2 |
| 2003/0025604 A1 * | 2/2003 | Freeman | 340/573.1 |
| 2003/0093503 A1 | 5/2003 | Yamaki et al. | |
| 2005/0035862 A1 * | 2/2005 | Wildman et al. | 340/573.1 |
| 2006/0116667 A1 * | 6/2006 | Hamel et al. | 606/1 |
| 2007/0107068 A1 * | 5/2007 | Kelley et al. | 726/34 |

(Continued)

FOREIGN PATENT DOCUMENTS

WO    WO 01/85085 A3    11/2001

OTHER PUBLICATIONS

International Search Report and Written Opinion of the International Searching Authority, mailed Mar. 16, 2009 (17 sheets).

(Continued)

*Primary Examiner* — Jinsong Hu
*Assistant Examiner* — Dung Hong
(74) *Attorney, Agent, or Firm* — Flynn, Thiel, Boutell & Tanis, P.C.

(57) ABSTRACT

A network system prevents portable wireless remote control consoles from unintended activation of a medical device by determining if the console is located in a working space within a medical care room. Transceiver locator devices determine the position of the remote control consoles and send information to room control units indicating when a console is within the desired working space. The room control unit receives signals from the remote control console in the working space to control medical devices. The room control unit can also determine which of multiple remote control consoles within the working space is permitted to operate the medical devices. Each room control unit can send a presence output to the remote control console to enable use thereof. The remote control console can have an orientation sensor or a grip detector to prevent unintended operation thereof.

23 Claims, 6 Drawing Sheets

U.S. PATENT DOCUMENTS

2007/0161904 A1* 7/2007 Urbano .................. 600/459
2008/0303707 A1 12/2008 Larsen et al.

OTHER PUBLICATIONS

International Preliminary Report on Patentability and Written Opinion for corresponding PCT Application No. PCT/US2008/010974 dated Apr. 8, 2010.

U.S. Appl. No. 10/607,810, Applicant: Andrew J. Hamel, et al., filed Jun. 27, 2003 entitled Foot-Operated Control Console for Wirelessly Controlling Medical Devices.

U.S. Appl. No. 11/263,083, Applicant: Andrew J. Hamel, et al., filed Oct. 31, 2005 entitled Apparatus and Method for Synchronizing a Wireless Remote Control to a Central Control Unit So As to Allow Remote Control of a Medical Device Over a Secure Wireless Connection.

U.S. Appl. No. 11/025,652, Applicant: Andrew J. Hamel, filed Dec. 29, 2004 entitled System for Remotely Controlling Two or More Medical Devices.

U.S. Appl. No. 11/985,339, Applicant: Andrew J. Hamel, et al., filed Nov. 14, 2007 entitled System and Method for Automatically Powering on and Synchronizing a Wireless Remote Console to a Central Control Unit So As to Allow Remote Control of a Medical Device.

U.S. Appl. No. 12/284,056, Applicant: Andrew J. Hamel, et al., filed Sep. 18, 2008 entitled Wireless Hand-Control of a Device by Means of Wireless Button.

* cited by examiner

SYSTEM FOR PREVENTING UNINTENDED ACTIVATION OF A MEDICAL DEVICE BY A PORTABLE REMOTE CONTROL CONSOLE

CROSS REFERENCE TO RELATED APPLICATION

This application claims the benefit of U.S. Provisional Application Ser. No. 60/995,330, filed Sep. 26, 2007, which is incorporated herein by reference in its entirety.

FIELD OF THE INVENTION

The present invention relates to a system for preventing unintended activation of a medical device by a portable wireless remote control console by determining if the remote control console is located in a desired working space within a medical care room and/or by sensing if the remote control console is in a proper orientation for use.

BACKGROUND OF THE INVENTION

Wireless remote control devices or consoles for controlling medical devices in a surgical operating room eliminate the physical constraint of a wired remote control device having an electrical cord. A cord limits the operating distance of the wired remote control device from a central controller or the medical device to be controlled. Eliminating cords provides improved accessibility in a work area, such as a surgical operating room. A wireless remote control console, however, may under certain circumstances actuate a medical device remotely from the typical working space in an operating room. This situation can arise when a wireless remote control console that controls a central control unit for medical devices is carried outside of the working space (e.g., a room) while remaining within range wirelessly so that it still communicates with the control unit. For example, a wireless footswitch console for use in an operating room may still be capable of activating a surgical device or other medical device therein, even when the footswitch console is outside of the operating room.

Accordingly, the present invention encompasses an arrangement that allows a remote control console to operate a central control unit only while located in the desired working space. This invention further prevents the wireless remote control console from unintended communication with a different central control unit located in a different operating space. Finally, the remote control console of a further embodiment of the invention must be oriented properly or grasped by a user to control a medical or surgical device.

SUMMARY OF THE INVENTION

A system for preventing unintended activation of a medical device by a wireless portable remote control console includes transceiver locator devices within rooms of a medical building to detect the location of portable remote control consoles. A global network receives information on the location of the portable remote control consoles. If a portable remote control console is not sensed within an operating space within a medical care room by the transceiver locator devices, the global network prevents the aforesaid portable remote control console from communicating with a room control unit to operate any of the medical devices in the medical care room. In one embodiment, the remote control console is a footswitch console. The footswitch console is disabled from controlling a control unit for medical devices when the footswitch console is not oriented properly with respect to the floor. In another embodiment, the remote control console is a hand-carried console that is disabled from controlling a medical device when a hand grasping the console is not sensed. In another embodiment, the location of both the remote control console and the room control unit is determined by the global network and displayed on a monitor. In another embodiment wherein multiple remote control consoles are provided, the console having the greatest signal strength or a special signal code overrides all other remote control consoles and is the only console allowed to control at least one of the medical devices in the medical care room.

BRIEF DESCRIPTION OF THE DRAWINGS

One or more embodiments of the present invention are illustrated by way of example and should not be construed as being limited to the specific embodiments depicted in the accompanying drawings, in which like references indicate similar elements and in which.

DETAILED DESCRIPTION

Figure 1:
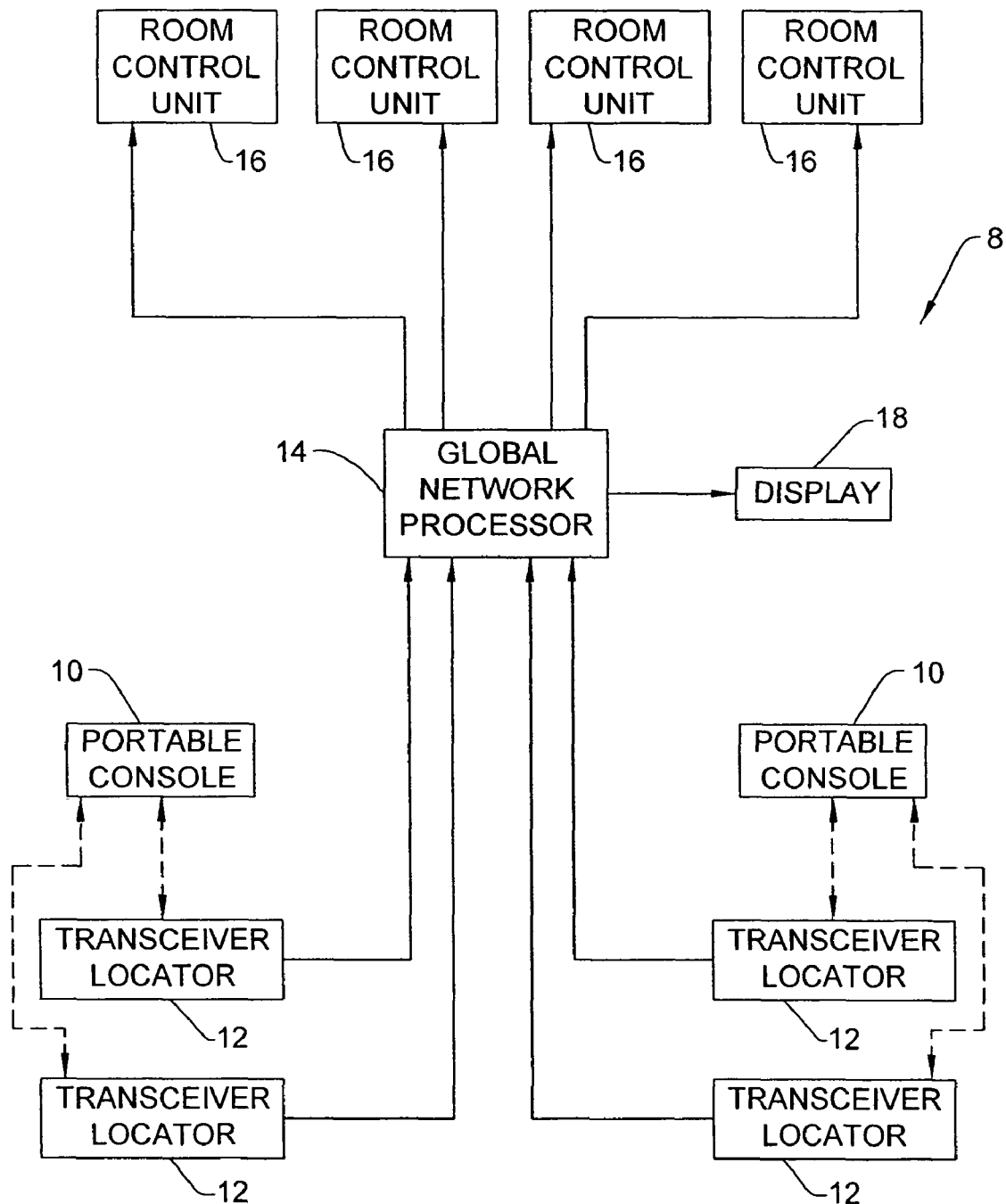
FIG. 1 is a block diagram of a global network system that includes transceiver locator devices for sensing wireless portable remote control consoles and for providing outputs to a global network processor according to one embodiment of the invention.

FIG. 1 depicts a block diagram of a global network system 8 according to one embodiment of the present invention. Portable wireless remote control consoles 10 are provided for controlling medical devices in a medical care room. Transceiver locator devices 12 are provided at predetermined locations to detect the presence of the portable remote control consoles 10. A global network processor 14 is provided to receive outputs from the transceiver locator devices 12. Room control units 16 that control medical devices in the medical care rooms receive data output from the global network processor 14. Each room control unit 16 can be a portable cart-based unit that is movable or a fixed control unit permanently located in a room. A display monitor 18 connected to the global network processor 14 can display the status or location of various portable control consoles 10 as explained in detail later with respect to the embodiments illustrated in FIGS. 2 and 3.

Figure 2:
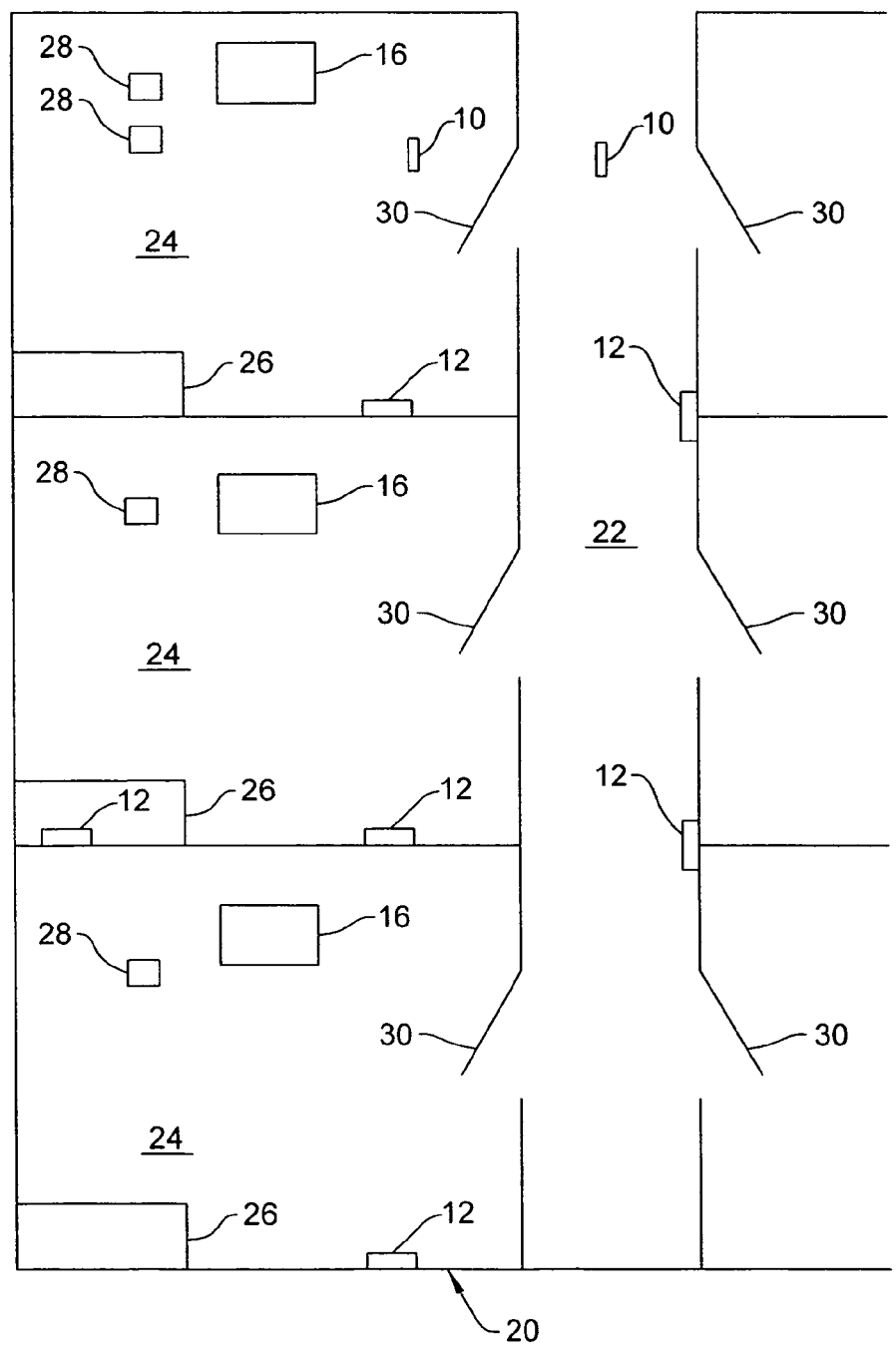
FIG. 2 illustrates a partial diagram of a medical building showing the arrangement of the system in medical care rooms and including transceiver locator devices to detect remote control consoles according to another embodiment of the invention.

The embodiment of FIG. 2 is illustrated by a partial diagram of a medical building 20 having a hallway 22 and individual rooms 24. The individual rooms 24 have storage closets 26 and entry doors 30. As shown in FIG. 2, transceiver locator devices 12 are selectively mounted in hallways 22, medical care rooms 24, closets 26 within the rooms 24, and throughout the medical building 20. One or more medical devices 28 are provided in selected ones of the rooms 24. The various medical devices 28 may include a high intensity light source that transmits light through an endoscope, a camera head for an endoscope, an insufflator, an electrocautery tool, various powered tools to cut or shape body tissues, and other surgical or medical devices not described herein.

In operation, the FIG. 2 embodiment for the network system 8 of FIG. 1 utilizes the transceiver locator devices 12 to detect the presence/location of the portable remote control consoles 10. The transceiver locator devices 12 rely on a time-of-flight arrangement to detect the location of remote control consoles 10. In one embodiment, the time-of-flight radio location system is similar to the system disclosed in U.S. Pat. No. 5,661,490, the disclosure of which is hereby incorporated by reference. In another embodiment, each portable remote control console 10 includes therein a transceiver or the like that receives an output from the transceiver locator devices 12 and returns a time-of-flight output signal to the transceiver locator devices 12. The transceiver locator devices 12 then transmit a wireless time-of-flight information signal or output to the global network processor 14. One or more of the transceiver locator devices 12 can detect the same portable remote control console 10. Further, one transceiver locator device 12 can detect more than one portable remote control console 10.

Global network processor 14 processes the time-of-flight outputs provided thereto by the transceiver locator devices 12 as wireless information signals. The global network processor 14 includes map data stored therein relating to the predetermined locations of the transceiver locator devices 12 throughout the medical care building 20 and the locations of walls/rooms within the medical care building. Thus, the global network processor 14 calculates the location of each detected portable remote control console 10 within the medical building 20.

After determining the locations of consoles 10, the global network processor 14 outputs data or information to the room control units 16. The data indicates the presence and/or absence of specific remote control consoles 10 in respective working spaces. The data enables the room control units 16 to recognize and respond only to inputs from the specific portable remote control console(s) 10 that are located within a desired working space for the specific room control unit 16. Other remote control consoles 10 not located within the desired working space can not control the specific room control unit 16. Each room control unit 16 can indicate which remote control consoles 10 are enabled to send control signals thereto, and which medical care devices 28 are operable by the remote control consoles.

In one embodiment, when a portable remote control console 10 is stored on a shelf in a closet 26, the global network processor 14 calculates a console location and determines that the stored console is not intended for use and informs the corresponding room control unit 16 to ignore any inputs received from the stored remote control console.

In one embodiment, the global network system 8 can store priority control data for each of the portable remote control consoles 10. Thus when a plurality of portable remote control consoles 10 are in the working space in a medical care room 24, the network processor 14 can send signals to the room control unit 16 indicating which remote control console 10 is permitted to operate which medical device 28. In one embodiment, a single portable remote control console 10 has sole and universal control of all of the medical devices 28 in the medical care room 24. In another embodiment, one portable remote control console 10 within the working space has sole and exclusive control over one medical device 28 and a second portable remote control console 10 within the working space has sole and exclusive control over a second medical device 28.

In another embodiment, the room control unit 16 either stores therein or receives identification data from the global network system 8 for each of the remote control consoles 10 in the respective medical care room 24. The global network or the room control unit 16 can store therein a hierarchy of values for each of the portable remote control consoles to determine which remote control console 10 in a working space, if any, should have sole and exclusive control of a select medical device 28 in a medical care room 24. In another embodiment, the room control unit 16 measures the signal strength for each portable remote control console 10 in a working space, and permits sole and exclusive control of one or more of the medical devices 28 by the remote control console 10 having the greatest signal strength. In another embodiment, two or more of the portable remote control consoles 10 in the working space of a medical care room 24 are capable of controlling the same medical device 28. In another embodiment, one of a plurality of portable remote control consoles 10 in the working space of a medical care room 24 has sole and universal control over all of the medical devices 28 in the medical care room.

Figure 3:
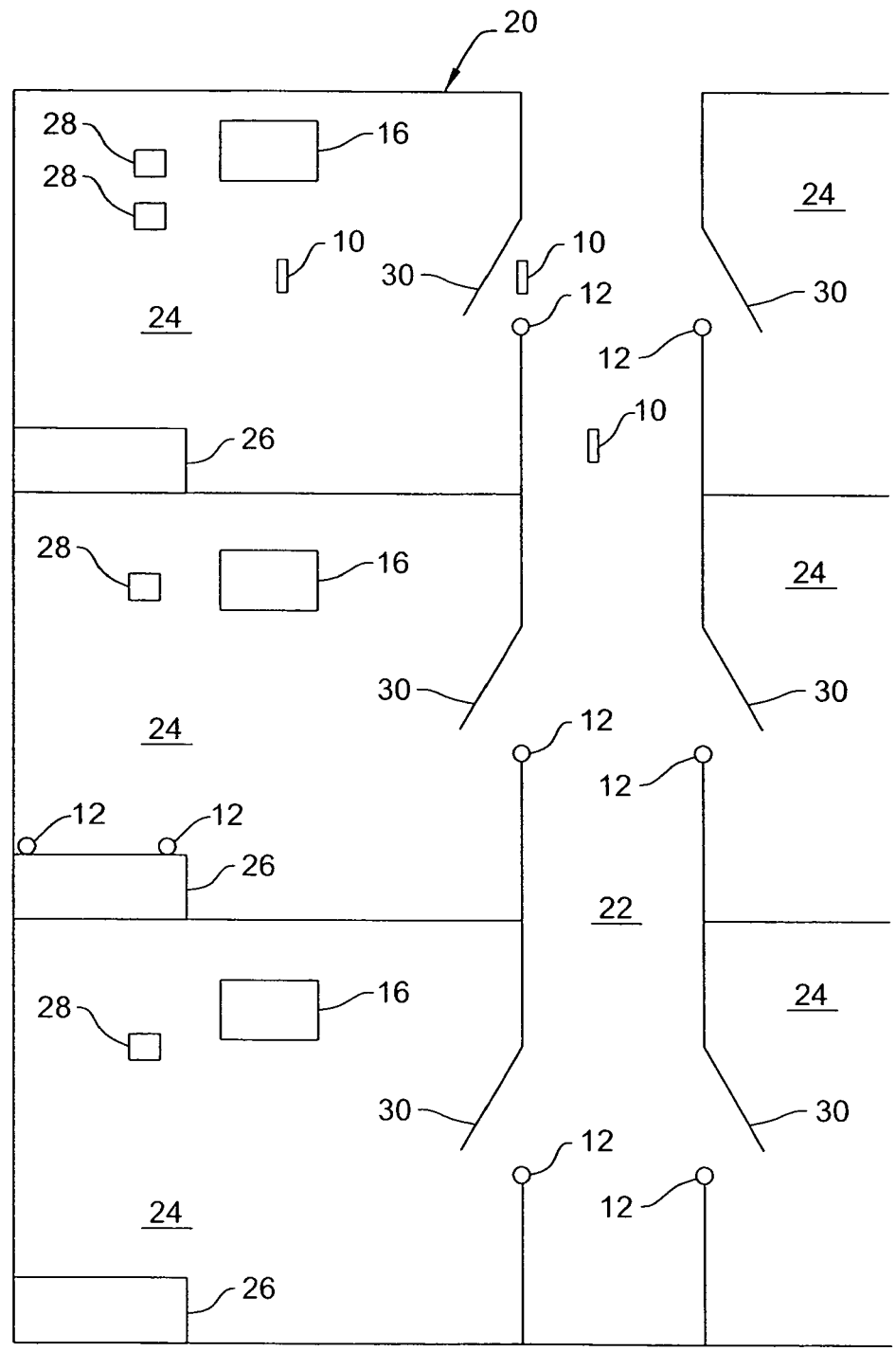
FIG. 3 illustrates a partial diagram of a medical building showing the arrangement of the system in medical care rooms and including transceiver locator devices at entrances of the medical care rooms according to another embodiment of the invention.

FIG. 3 is an embodiment similar to FIG. 2 as described above, except the transceiver locator devices 12 are mounted mainly at or about entrances of the doors 30 of the medical care rooms 24. The transceiver locator devices 12 are also provided for select closets 26 to determine when a remote control console 10 is placed therein.

In the embodiment of FIG. 3, the transceiver locator devices 12 each use proximity sensing to detect the presence and the direction of movement of the portable remote control consoles 10 as they are carried into and out of medical care rooms 24. In one embodiment, the transceiver locator devices 12 are mounted at or about respective doors 30. Each transceiver locator device 12 includes both a radio frequency transmitter that outputs a radio frequency and a receiver/detector. The output radio frequency is received by an RFID chip located in each portable remote control console 10. The RFID chip that receives the radio frequency then outputs a return signal to the locator device 12 identifying the specific portable remote control console 10 that is entering or exiting through the door 30. The transceiver locator device 12 then provides an output to the global network processor 14, including data regarding the detected portable control console 10. At this stage, the embodiment of FIG. 3 operates in essentially the same manner as the embodiment of FIG. 2 described above. The global network processor 14 informs the specific room control unit 16 of the presence of the specific remote control console 10 in the working space of the corresponding medical care room 24.

Other types of transceiver locator devices 12 than the embodiments disclosed in FIGS. 2 and 3 are contemplated by the invention. The block diagram of FIG. 1 shows lines defining connections between the global network processor 14 and both the transceiver locator devices 12 and the room control units 16. In some embodiments, the network processor 14 has wireless connections with the transceiver locator devices 12 and the room control units 16. In other embodiments the connections are wired connections.

Figure 4:
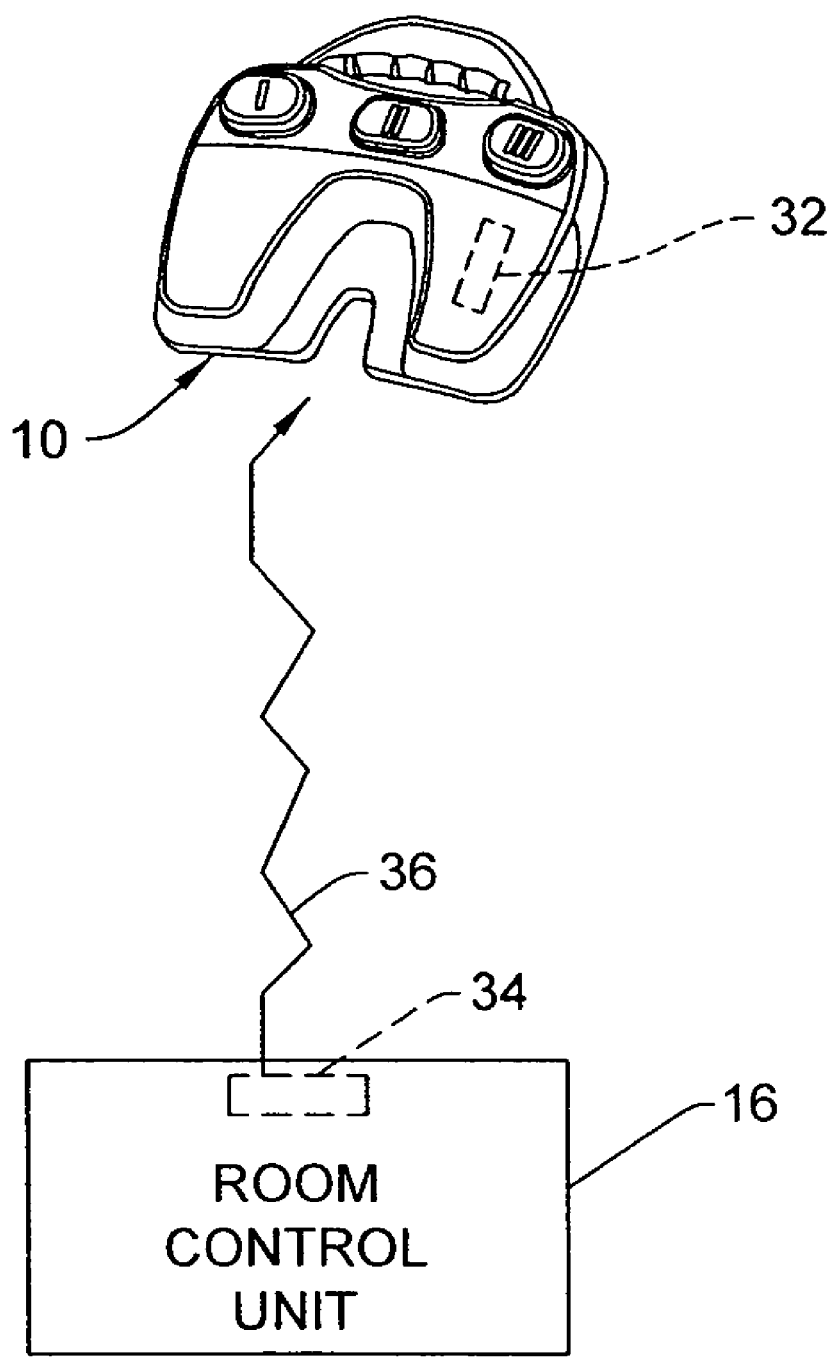
FIG. 4 illustrates a room control unit and a wireless portable remote control console according to another embodiment of the invention.

FIG. 4 depicts an embodiment of the invention wherein the portable remote control console 10 comprises a wireless portable remote control footswitch console. The footswitch console 10 is a variation of the footswitch console disclosed in commonly owned U.S. patent application Ser. No. 10/607,810 filed Jun. 27, 2003, corresponding to U.S. Pat. Pub. 2008/0140158, the disclosure of which is hereby incorporated by reference in its entirety. The footswitch console 10 includes an enabling receiver 32 as illustrated by broken line in FIG. 4. The room control unit 16 of FIG. 4 includes a presence transmitting device 34 as illustrated by broken line that transmits a control unit presence output 36.

In operation, the room control unit 16 provides the presence output 36 for detection by the enabling receiver 32. The enabling receiver 32 of the footswitch console 10 detects the presence output 36. To avoid unintended activation, the footswitch console 10 only sends medical device control signals to the room control unit 16 when the presence output 36 is detected. Therefore, the footswitch console 10 is disabled from controlling any medical device 28 unless the presence output 36 from the room control unit 16 is detected.

In one embodiment of the invention, the presence transmitting device 34 is an infrared transmitter that outputs an infrared beam 36. The enabling receiver 32 is an infrared receiver for detecting an infrared beam. In this embodiment, the infrared receiver 32 must detect the infrared beam 36 to enable operation of the corresponding footswitch console 10.

In another embodiment of the invention, the presence transmitting device 34 is an ultrasonic transducer that provides an ultrasonic output 36 that is above the human audible range. The enabling receiver 32 is an ultrasonic detector for detecting the ultrasonic output 36. In this embodiment, the ultrasonic detector 32 detects the ultrasonic output 36 to enable operation of the corresponding footswitch console 10. Absent detection of the ultrasonic output 36, the footswitch console 10 is disabled and thus unable to control any medical device 28 in the medical care room 24.

In another embodiment of the invention, the room control unit 16 can provide the presence output 36 to a plurality of footswitch consoles 10 having enabling receivers 32 and to handheld portable remote control consoles 10 having enabling receivers. The room control unit 16 can then control medical devices 28 based on the greatest output signal strength received from a footswitch console 10 or from a handheld portable remote control console 10 in the medical care room 24. In other embodiments, the room control unit 16 determines the specific portable remote control consoles 10 in a working space providing inputs thereto and, depending on predetermined hierarchy information stored therein, enables one of the remote control consoles 10 to have sole and exclusive control over one or more of the medical devices 28. Further, sole and universal control, or predetermined shared control can be provided for selected remote control consoles 10 as discussed above.

Figure 5:
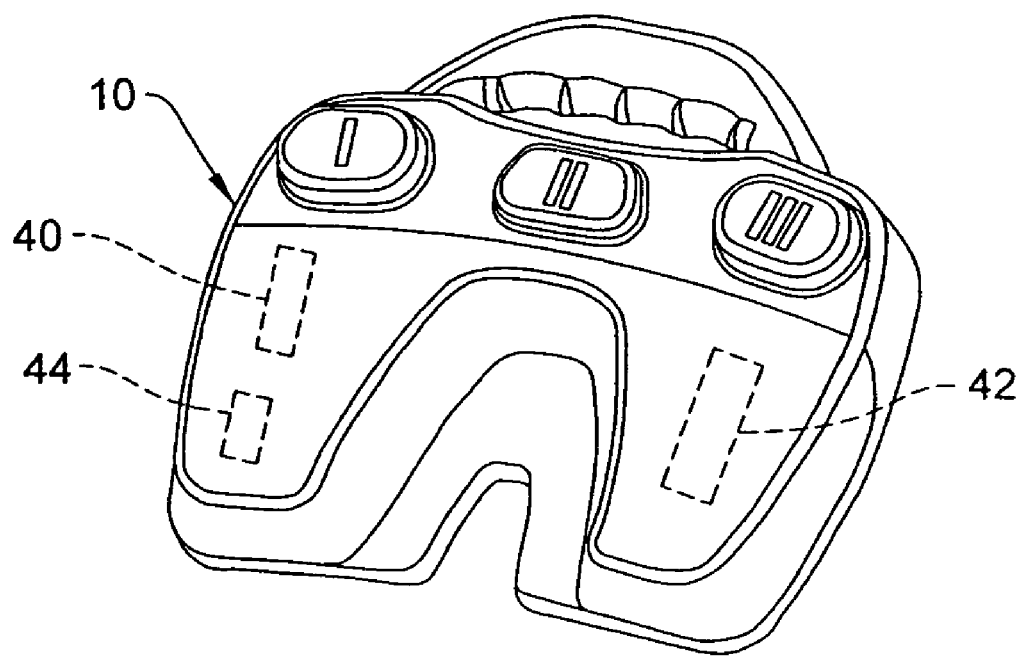
FIG. 5 illustrates a wireless footswitch remote control console according to another embodiment of the invention.

FIG. 5 illustrates another embodiment of the portable wireless remote control footswitch console 10. In this embodiment, the footswitch console 10 includes features to prevent unintended operation of a medical device 28. More specifically, the footswitch console 10 includes a tilt sensor 40 illustrated by broken line in FIG. 5. The tilt sensor 40 senses when the footswitch console 10 is not oriented in a generally horizontal position corresponding to a use location on the floor surface of a medical care room 24. When the tilt sensor 40 determines the footswitch console 10 is not properly oriented, for example due to being carried by a user in a substantially vertical orientation or stored in a non-horizontal orientation, the footswitch console is disabled from transmitting medical device control signals to the room control unit 16. Thus, the footswitch console 10 cannot control medical devices 28 in the medical care room 24 unless properly oriented.

Another embodiment of the invention illustrated in FIG. 5 includes an accelerometer 42 shown in broken line within the footswitch console 10. In this embodiment, the accelerometer 42 detects a sudden acceleration or deceleration force. After detecting the force, the accelerometer 42 prevents the footswitch console 10 from transmitting control signals to the room control unit 16 for a predetermined time period. In operation, if the portable footswitch console 10 is dropped by a user, regardless of the orientation of the console, the impact force caused by hitting the floor disables the footswitch console for a predetermined time. Thus, the accelerometer 42 prevents an unintended actuation of a medical device 28.

Other embodiments of the invention include a floor sensor 44 shown in broken line in FIG. 5 for sensing that the footswitch console 10 is placed on a generally flat horizontal surface. In one embodiment, the floor sensor 44 is a mechanical switch that is actuated by the weight of the footswitch console body. In another embodiment, the floor sensor 44 of the footswitch console 10 is a light source and light sensor. In this embodiment, reflected light is detected to determine that the lower face of the footswitch console 10 is adjacent a floor surface. In yet another embodiment, the floor sensor 44 is an acoustic sensor that outputs an acoustic wave and detects the reflection thereof from the floor surface to determine that the lower face of the footswitch console 10 is adjacent the floor surface. In all of the embodiments the floor sensor 44 prevents the footswitch console 10 from controlling a medical device 28 unless the footswitch console is properly oriented on a flat floor surface.

Figure 6:
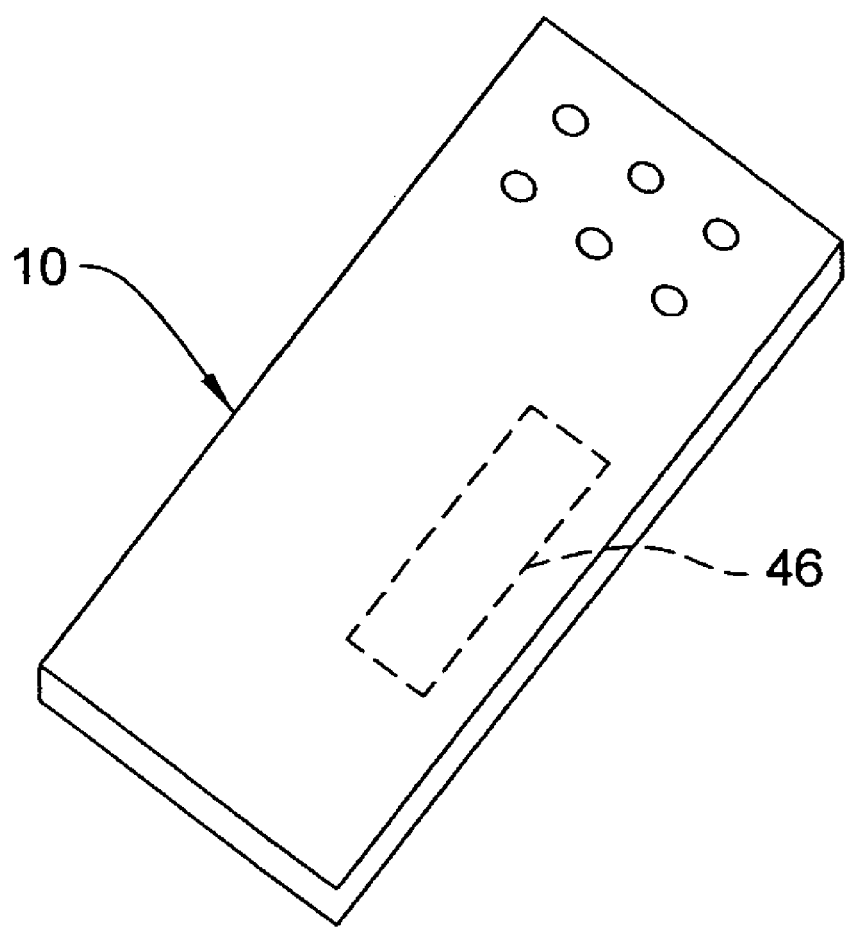
FIG. 6 illustrates a wireless handheld remote control console according to another embodiment of the invention.

While the embodiments of FIGS. 4 and 5 provide a footswitch console 10, any other type of remote control console is contemplated, such as a portable wireless hand held remote control console as shown in FIG. 6.

In the FIG. 6 embodiment, the handheld remote control console 10 includes a grip detector 46 as represented by broken line. The grip detector 46 detects grasping of the handheld remote control console 10 or the presence of a user's hand holding the remote control console. In one embodiment of the invention, the grip detector 46 includes one or more pressure sensors that detect the pressure applied to the handheld console 10 by the grasp of a user. In another embodiment, the grip detector 46 includes one or more of capacitive, inductive and resistive sensor(s) that sense impedance changes in an electromagnetic field caused by the presence of a user's hand. Other known hand detecting arrangements are also contemplated.

In another embodiment, each room control unit 16 is located on a movable cart for allowing the room control units to be moved between medical care rooms 24. Each cart based room control unit 16 includes a cart transceiver that interacts with the transceiver locator devices 12 so that the global network processor 14 can monitor the location of the cart based room control units. The display monitor 18 selectively displays the location of each cart based room control unit 16 and/or each portable remote control console 10.

Although the present invention has been described with reference to specific exemplary embodiments, it will be recognized that the invention is not limited to the embodiments described, but can be practiced with modification and alteration within the spirit and scope of the appended claims.

Accordingly, the specification and drawings are to be regarded in an illustrative sense rather than a restrictive sense.

What is claimed is:

1. A system for preventing unintended activation of a medical device located in a medical room by portable wireless remote control consoles, said system comprising:

room control units provided in at least two medical rooms of the medical care building;
medical devices disposed within each of the at least two medical rooms;
a plurality of transceiver locator devices disposed at predetermined locations within a medical care building including within or adjacent at least two of said medical rooms; and
a global network including a global network processor connected to said plurality of transceiver locator devices for receiving inputs from the transceiver locator devices to determine the locations of the portable wireless remote control consoles in the medical care building, said global network processor being connected to said room control units for providing outputs to the room control units indicating which if any of said portable wireless remote control consoles are within the corresponding room, wherein the room control unit is capable of identifying the medical devices in the corresponding room that are controllable by said portable remote control consoles within the corresponding room, and when one of the portable wireless remote control consoles is sensed outside of an operating space within a medical room by the transceiver locator devices, the system prevents the one portable remote control console from operating any of the medical devices in said medical room.

2. The system of claim 1, the medical devices including at least one of an electrocautery tool, a radio frequency generator and a cutter/shaver tool, wherein the transceiver locator devices transmit RF signals that are received by the portable remote control consoles, which then transmit a return signal for receipt by the transceiver locator devices; and
wherein the transceiver locator devices transmit a wireless information signal to the global network processor in response to the return signal.

3. The system of claim 2, wherein the transceiver locator devices utilize a time of flight arrangement to determine the position of each said portable remote control console within the medical care building.

4. The system of claim 2, wherein each said portable remote control console includes an RFID element therein for receiving the RF signals.

5. The system of claim 1, wherein said transceiver locator devices are located at the doorways of the medical rooms to determine when the portable remote control consoles enter or exit from the respective medical room, said portable wireless remote control consoles each having a plurality of controls including a selection control to allow a user to select a device to be controlled from the medical devices.

6. The system of claim 1, wherein said portable remote control consoles comprise wireless footswitch consoles for controlling medical devices within the medical room.

7. The system of claim 6, wherein said footswitch consoles each include a tilt sensor to prevent actuation of the footswitch console when said footswitch console is not oriented properly.

8. The system of claim 6, wherein said footswitch consoles each further comprise an accelerometer mounted therein to prevent actuation of one of the medical devices for a predetermined time when a sudden force is applied to said footswitch console.

9. The system of claim 1, wherein said transceiver locator devices are positioned so that a position for one of the portable remote control consoles disposed within a medical room is determined by the global network processor, the global network processor providing outputs to the respective room control unit to prevent operation of a medical device by the one remote control console when the global network processor determines the one remote control console is located in a storage space within the medical room.

10. The system of claim 1, wherein said portable remote control consoles comprise hand carried remote control consoles having a grip detector to prevent operation when a user loses grasp of one of the hand carried remote control consoles.

11. The system of claim 10, wherein said grip detector comprises at least one of an inductance sensor, capacitance sensor and resistance sensor for sensing the presence of a hand of a user.

12. The system of claim 1, wherein said room control units comprise movable cart-based room control units for wirelessly controlling a plurality of medical devices located in the corresponding medical room.

13. The system of claim 12, wherein each said movable cart-based room control unit includes a cart transceiver that interacts with said transceiver locator devices connected to said global network processor so that the global network is capable of monitoring the location of each said cart-based room control unit in said medical care building.

14. The system of claim 13, wherein said global network includes a display monitor for displaying the location of each said cart-based room control unit and each said portable remote control console within the medical care building.

15. The system of claim 1, wherein when the global network identifies a plurality of said portable wireless remote control consoles located within one said medical room, said global network processor provides outputs to the room control unit so that one of said portable wireless remote control consoles within the working space within the medical room is provided with sole and exclusive control of at least one of the medical devices.

16. The system of claim 15, wherein said portable wireless remote control consoles each include a unique identification signal to provide a predetermined control value that is defined within a hierarchy so that, depending on control values of said portable wireless remote control consoles located in the medical room, the one of said wireless remote control consoles is provided with the sole and exclusive control over the at least one of the medical devices in the medical room and a second one of said wireless remote control consoles is provided with sole and exclusive control over a second said medical device.

17. The system of claim 1, wherein when the global network identifies a plurality of said portable wireless remote control consoles located within said medical room, said global network processor provides outputs to the room control unit so that one of said portable wireless remote control consoles within the medical room is provided with sole and exclusive control of at least a first one of the medical devices, and a second one of said portable wireless remote control consoles within the working space within the medical room is provided with sole and exclusive control of at least a second one of the medical devices.

18. The system of claim 1, wherein each said room control unit includes a transceiver that interacts with said transceiver locator devices connected to said global network processor so that the global network is capable of monitoring the location of each said room control unit in said medical care building.

19. A system for preventing unintended activation of a medical device located in a medical room by a portable wireless remote control console, said system comprising:
room control units provided in at least two medical rooms of the medical care building;

medical devices disposed within each of the at least two medical rooms, the medical devices in each of the medical rooms being in communication with the respective room control unit provided in the medical room;

portable wireless remote control consoles, each said console having a plurality of controls including a selection control to allow a user to select a device to be controlled from the medical devices;

a plurality of transceiver locator devices disposed at predetermined locations within a medical care building including within or adjacent at least two of said medical rooms, the transceiver locator devices transmitting RF signals that are received by the portable remote control consoles, which then transmit a return signal for receipt by the transceiver locator devices; and a global network including a global network processor connected to said plurality of transceiver locator devices for receiving wireless information signals transmitted by the transceiver locator devices in response to the return signals to determine the locations of the portable wireless remote control consoles in the medical care building, said global network processor being in communication with said room control units for providing outputs to the room control units indicating Which if any of said portable wireless remote control consoles are within the corresponding room, wherein the room control unit is capable of identifying the medical devices in the corresponding room that are controllable by said portable remote control consoles within the corresponding room, and when one of the portable wireless remote control consoles is sensed outside of an operating space within a medical room by the transceiver locator devices, the system prevents the one portable remote control console from operating any of the medical devices in said medical room even when the one remote control console is within RF range of the room control unit.

20. The system of claim 19, wherein each said room control unit comprises a portable room control unit for wirelessly controlling a plurality of medical devices located in the corresponding medical room, wherein said transceiver locator devices transmit RF signals that are received by said portable remote control units which then transmit a return signal for receipt by the transceiver locator devices connected to said global network processor, so that the global network is capable of monitoring the location of each said room control unit in said medical care building.

21. The system of claim 20, wherein each said portable remote control console comprises a wireless footswitch console having a plurality of controls including a selection control to allow an operator to select one of said medical devices within the corresponding medical room to be controlled from among the medical devices, the medical devices disposed within the corresponding medical room including at least one of an electrocautery tool, a radio frequency generator and a cutter shaver tool.

22. A method of preventing unintended activation of a medical device located in a medical room by portable wireless remote control consoles, the method comprising:

providing room control units and medical devices disposed in at least two medical rooms of a medical care building;

providing a plurality of transceiver locator devices disposed at predetermined locations within a medical care building including within or adjacent at least two of the medical rooms;

sending inputs from the transceiver locator devices to a global network including a global network processor;

determining the locations of the portable wireless remote control consoles in the medical care building;

sending outputs from the global network processor to the room control units indicating which, if any, of the portable wireless remote control consoles are within the corresponding medical room;

identifying the medical devices in the corresponding room with the room control unit that are controllable by the portable wireless remote control consoles; and after sensing that one of the portable wireless remote control consoles is located outside of an operating space within a medical room, preventing the one portable wireless remote control console from operating any of the medical devices in the medical room.

23. A method of preventing unintended activation of a medical device located in a medical room by a portable wireless remote control console, the method comprising:

providing room control units and medical devices within at least two medical rooms of a medical care building, the medical devices in each of the medical rooms being in communication with the respective room control unit;

providing portable wireless remote control consoles, each of the consoles having a plurality of controls including a selection control to allow a user to select a medical device to be controlled from the medical devices;

providing a plurality of transceiver locator devices disposed at predetermined locations within a medical care building including within or adjacent the at least two medical rooms;

transmitting RF signals from the transceiver locator devices to the portable wireless remote control consoles;

transmitting a return signal from the portable wireless remote control consoles for receipt by the transceiver locator devices in response to the RF signals;

in response to the return signals, transmitting wireless information signals from the transceiver locator devices to a global network including a global network processor;

determining the locations of the portable wireless remote control consoles in the medical care building;

providing outputs to the room control units from the global network processor indicating which, if any, of the portable wireless remote control consoles are located within the corresponding medical room, identifying the medical devices in the corresponding room with the room control unit that is controllable by the portable wireless remote control consoles; and after sensing that one of the portable wireless remote control consoles is located outside of an operating space within a medical room, preventing the one portable remote control console from operating any of the medical devices in the medical room even when the one remote control console is within RF range of the room control unit.

* * * * *

UNITED STATES PATENT AND TRADEMARK OFFICE
CERTIFICATE OF CORRECTION

PATENT NO.         : 8,175,590 B2
APPLICATION NO.    : 12/283808
DATED              : May 8, 2012
INVENTOR(S)        : Andrew J. Hamel et al.

It is certified that error appears in the above-identified patent and that said Letters Patent is hereby corrected as shown below:

Column 9, line 24; replace "Which if any" with --which if any--.

Signed and Sealed this
Tenth Day of July, 2012

David J. Kappos
*Director of the United States Patent and Trademark Office*